United States Patent [19]

Cristensen

[11] 4,172,385
[45] Oct. 30, 1979

[54] SAMPLING DEVICE FOR SEPTIC TANKS
[76] Inventor: Melford K. Cristensen, 2637 Wayside La., Springfield, Oreg. 97477
[21] Appl. No.: 916,793
[22] Filed: Jun. 16, 1978
[51] Int. Cl.² .............................................. G01N 1/12
[52] U.S. Cl. .............................................. 73/425.4 R
[58] Field of Search ............. 33/126.4 R; 73/425.4 R
[56] References Cited
U.S. PATENT DOCUMENTS

| 455,733 | 7/1891 | Bell | 33/126.4 R |
|---|---|---|---|
| 1,296,794 | 3/1919 | Haggstrom | 73/425.4 |
| 2,634,612 | 4/1953 | Quist | 73/425.4 R |

Primary Examiner—S. Clement Swisher
Attorney, Agent, or Firm—James D. Givnan, Jr.

[57] ABSTRACT

A transparent tube is provided with a closure plate at its lower end with the plate including a resilient pad for sealing engagement with the tube end. A plate control rod extends lengthwise along the tube and terminates upwardly in a handle which is perpendicularly disposed on the control rod in the same direction as the closure plate to permit handle to serve as an indicator of the open or closed status of the submerged end of the tube. A spring component biases the control rod and closure plate upwardly to seal the tube lower end thereby confining the vertical cross sectional sample in the tube during sample evaluation.

3 Claims, 4 Drawing Figures

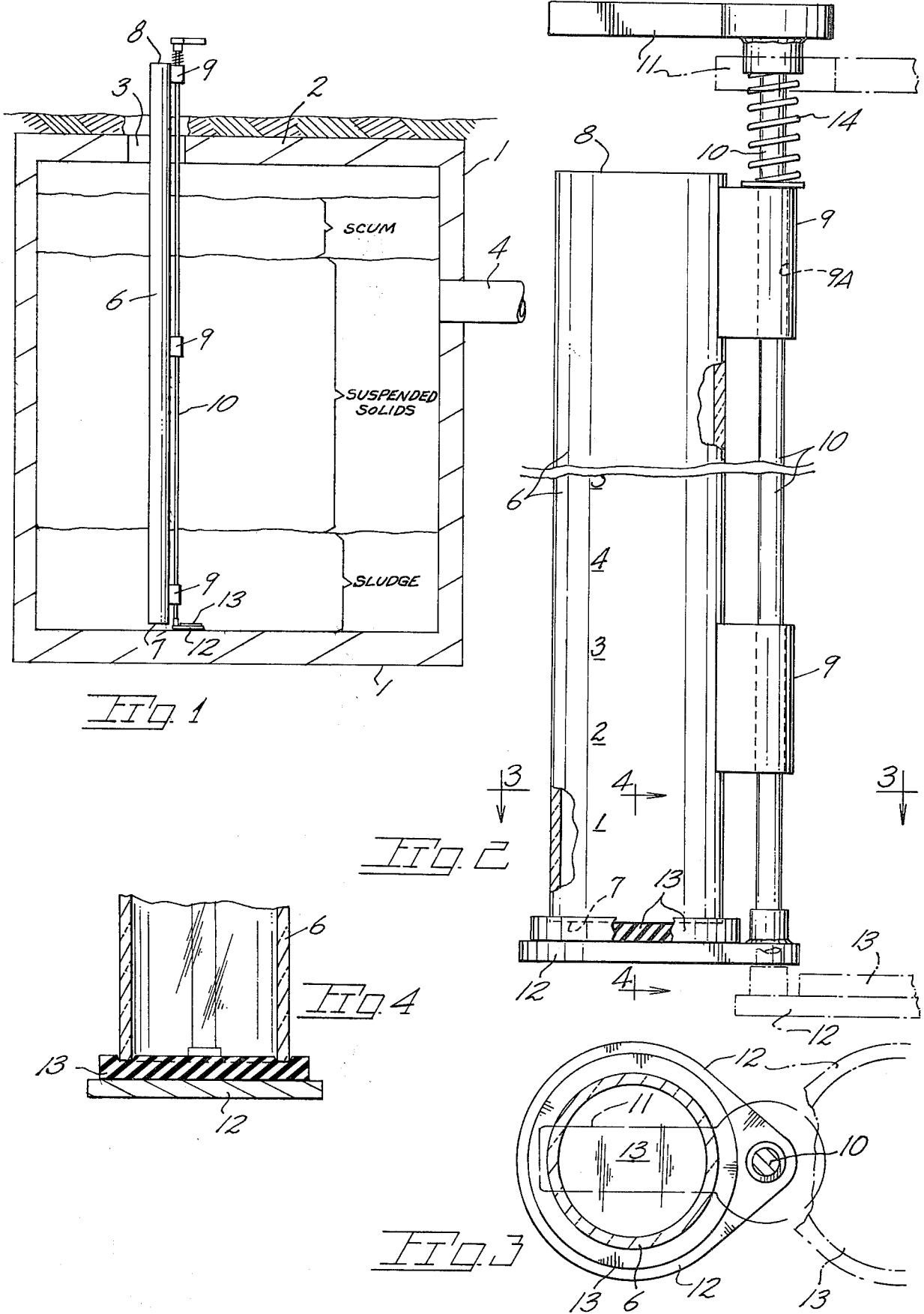

SAMPLING DEVICE FOR SEPTIC TANKS

BACKGROUND OF THE INVENTION

The present invention relates generally to tank sampling devices and particularly to such a device for taking a vertical sample of septic tank contents.

Proper maintenance of a septic tank entails periodic removal of the tank contents to assure proper operation of the tank and its associated drain field. As it is not possible to determine the amoung of sludge or suspended sewage in a tank by viewing same through the tank opening, tanks are sometimes unnecessarily pumped at considerable cost to the homeowner. Conversely, the homeowner will occasionally put off pumping of a septic tank permitting tank sludge to enter the septic tank drain field to destroy or at least inhibit the drain field's capability to desperse septic tank discharge and may require the laying of a new drain field at substantial expense.

SUMMARY OF THE PRESENT INVENTION

The present invention is embodied within a sampling device insertable lengthwise through a septic tank opening to take/a vertical, cross sectional sampling of tank contents.

The device includes a transparent tube of a cross section to freely admit septic contents as it is lowered into contact with the tank bottom wall. At the tube lower end is a closure plate adapted to positively seal the tube lower end prior to extraction from the tank. For sealing purposes the closure plate includes a resilient pad biased upwardly by a spring component acting on a plate supporting control rod. Said rod is supported along the tube for both rotational and axial movement. A handle at the rod's upper end is offset from the rod in the same direction as said plate so as to additionally serve as an indicator of the plate position when the tube is partially submerged within a tank.

Important objectives of the present invention include the provision of a sampling device intended for taking a vertical sample of septic tank contents for the purpose of apprising the homeowner of the tank condition and whether or not pumping out of the tank is necessary; the provision of a sampling device including a transparent tubular component providing a visual indication of the sludge depth, depth of suspended sewage and scum within a septic tank; the provision of an inexpensive sampling device which assures retention of the sample when withdrawn from the tested material and oppositely permits convenient return of the material to the tested body after sampling; the provision of a septic tank testing device permitting convenient evaluation of septic tank condition and avoidance of damage to drain fields by excessive accumulations of tank sludge.

BRIEF DESCRIPTION OF THE DRAWINGS

In the accompanying drawing:

FIG. 1 is a side elevational view of the present device inserted within a septic tank shown in section;

FIG. 2 is an enlarged side elevational view of the present device sectioned for purposes of illustration;

FIG. 3 is a horizontal sectional view taken along line 3—3 of FIG. 2; and

FIG. 4 is a vertical sectional view taken along line 4—4 of FIG. 2 showing details of the closure plate.

DETAILED DESCRIPTION OF THE PREFERRED EMBODIMENT

With continuing attention to the drawing, the reference numeral 1 indicates a typical septic tank having a top wall 2 defining an access opening 3. Typically such tanks include a discharge conduit as at 4 which leads to branched conduits of a drain field.

Tank contents are generally classified from bottom to top as sludge, suspended sewage and scum. For proper tank operation the sludge level must be retained below the discharge conduit 4 to prevent entry of sludge into the drain field.

With attention now to the present device, the same includes a tube 6 of transparent material, at least for a major portion of its length and open at its lower end 7 as well as at its top end 8. Desirably, the tube should have an inside diameter of approximately 6 cm to facilitate reception and discharge of the tested material. Located along the tube length are bosses 9 which define opening 9A within which is slidably and rotatably received a plate control rod 10.

The rod 10 extends somewhat beyond the upper end of tube 6 and is thereat provided with a handle 11 to enable the manual imparting of both axial as well as rotational movement to the rod. At the lower end of said rod is a closure plate 12 disposed perpendicularly to the tube axis and provided with a resilient pad 13 which is preferably of soft rubber or the like.

Biasing control rod 10 and plate 12 carried thereby is a helical spring 14 interposed between the uppermost boss 9 and handle 11. Accordingly spring 14 normally serves to urge resilient pad 13 into sealing engagement with the tube lower end to prevent the escape of any material stored within the tube during tank evaluation.

As viewed in FIG. 2, it will be noted that handle 11 is offset in the same direction as plate 12 from the axis of rod 10 to enable the handle to serve to indicate when plate 12 and pad 13 thereon are in sealing engagement with the tube lower end. Accordingly the user of the present device need only assure the diametric positioning of handle 11 to the subjacent upper end of the tube and handle release to verify closure of the tube lower end prior to extraction of the device from the tank.

In use the device is inserted lengthwise through tank opening 3 with closure plate 12 swung to the closed position and the tube lower end inserted past the lower level of the scum layer whereupon the closure plate is swung to the open position. Lifting of the tube with the plate in the open position will provide an indication of the scum layer depth as plate contact with the underside of the layer will be detected by increased resistance to lifting of the tube. The user then takes note of the inch increments on the side of the tube to determine scum level thickness or depth. The plate is then swung to the open position shown in broken lines in FIG. 2. To accomplish such positioning, a downward force is exerted on handle 11 to disengage pad 13 from the tube end whereupon handle 11 and plate 12 are simultaneously rotated one-half turn. Upon contact with the tank bottom wall, tube end 7 is closed by return positioning of the handle and plate entailing rotational movement of handle 11 back through 180 degrees. As earlier noted, since the handle and plate are offset in the same direction from rod 10, the handle serves as an indicator of the plate position and whether or not the tube is open or closed at its lower end. With the tube lower end closed, the tube and its contents are withdrawn from the tank for evaluation of the vertical cross sectional sample. After evaluation, the tube is again deposited in the tank, the closure plate swung open for discharge of tube contents back into the tank.

While I have shown but one embodiment of the invention it will be apparent to those skilled in the art that the invention may be embodied still otherwise without departing rrom the spirit and scope of the invention.

Having thus described the invention, what is desired to be secured under a Letters Patent is:

1. A device for taking a vertical cross sectional sample of a septic tank, said device comprising,
    a tube of a transparent nature for a major portion of its length and having an unrestricted lower end,
    a closure plate engageable with the tube lower end including a resilient pad thereon,
    a control rod slidably and rotatably mounted along said tube and carrying said closure plate at the rod lower end, a handle on said rod in upwardly spaced relationship to the tube upper end, said closure plate and said handle offset in the same direction from the control rod axis to permit the handle to additionally serve as an indicator of plate position and hence the open or closed status of the tube's tank submerged lower end, and resilient means axially biasing said rod and thereby urging said closure plate into sealing engagement with the tube lower end to retain a sample therein.

2. The device claimed in claim 1 wherein said biasing means is a helical spring disposed about said rod and coacting with the tube.

3. The device claimed in claim 2 wherein said tube is open ended at top and bottom and includes bosses spaced therealong to receive said rod for both rotational and axial rod movement.

* * * * *